(12) United States Patent
Hatti-Kaul et al.

(10) Patent No.: US 9,546,147 B2
(45) Date of Patent: Jan. 17, 2017

(54) METHOD FOR PRODUCING CYCLIC CARBONATES

(76) Inventors: Rajni Hatti-Kaul, Lund (SE);
Sang-Hyun Pyo, Lund (SE)

(*) Notice: Subject to any disclaimer, the term of this patent is extended or adjusted under 35 U.S.C. 154(b) by 0 days.

(21) Appl. No.: 14/117,470

(22) PCT Filed: May 14, 2012

(86) PCT No.: PCT/SE2012/050513
§ 371 (c)(1),
(2), (4) Date: Nov. 13, 2013

(87) PCT Pub. No.: WO2012/158107
PCT Pub. Date: Nov. 22, 2012

(65) Prior Publication Data
US 2014/0235875 A1    Aug. 21, 2014

Related U.S. Application Data

(60) Provisional application No. 61/486,237, filed on May 14, 2011.

(30) Foreign Application Priority Data

Oct. 21, 2011   (SE) ..................................... 1150981

(51) Int. Cl.
| | | |
|---|---|---|
| *B01J 23/18* | (2006.01) | |
| *B01J 21/08* | (2006.01) | |
| *B01J 21/06* | (2006.01) | |
| *C07D 319/06* | (2006.01) | |
| *C07D 317/36* | (2006.01) | |
| *C07C 68/06* | (2006.01) | |

(52) U.S. Cl.
CPC ............ *C07D 319/06* (2013.01); *B01J 21/063* (2013.01); *B01J 21/08* (2013.01); *B01J 23/18* (2013.01); *C07C 68/06* (2013.01); *C07D 317/36* (2013.01)

(58) Field of Classification Search
CPC ..... C07D 317/36; C07D 319/06; C07C 68/06; C07C 69/96; C07C 319/06; B01J 23/18; B01J 21/08; B01J 21/063
USPC ................... 549/230, 228; 260/463; 558/265
See application file for complete search history.

(56) References Cited

U.S. PATENT DOCUMENTS

| | | | |
|---|---|---|---|
| 4,410,464 A * | 10/1983 | Hallgren ....................... 558/271 |
| 4,440,937 A | 4/1984 | Krimm et al. | |
| 4,880,942 A | 11/1989 | Kiso et al. | |
| 5,091,543 A | 2/1992 | Grey | |
| 5,436,362 A | 7/1995 | Kondoh et al. | |
| 5,861,107 A | 1/1999 | Buysch et al. | |
| 5,922,888 A * | 7/1999 | Toriida et al. ................ 549/228 |

FOREIGN PATENT DOCUMENTS

| | | |
|---|---|---|
| CN | 1569811 A | 1/2005 |
| EP | 0 139 442 A1 | 5/1985 |
| EP | 0 422 523 A2 | 4/1991 |
| EP | 0 735 034 A1 | 10/1996 |
| JP | 64-26576 A | 1/1898 |
| JP | 57-144282 | 9/1982 |
| JP | 10-059957 | 3/1998 |
| WO | 2009035269 A2 | 3/2009 |

OTHER PUBLICATIONS

Carothers, W. H., "Studies on polymerization and ring formation. III. Glycol esters of carbonic acid." Journal of the American Chemical Society 52(1) (1930): 314-326.*
Diethylcarbonate properties, http://en.wikipedia.org/wiki/Diethyl_carbonate; accessed online Jun. 19, 2014.*
Kresge, C.T., Molecular Sieves, Kirk-Othmer Encyclopedia of Chemical Technology 2004, vol. 16, p. 811-853.*
(Sigma-Aldrich Dimethyl carbonate product sheet; accessed online May 28, 2015 http://www.sigmaaldrich.com/catalog/product/sial/517127?lang=en&region=US; p. 1-4.*
Li, J. "Chemical equilibrium of glycerol carbonate synthesis from glycerol." The Journal of Chemical Thermodynamics 43.5 (2011): 731-736.*
International Search Report, dated Jul. 25, 2012, from corresponding PCT application.
Sang-Hyun Pyo et al., "Solvent-free lipase-mediated synthesis of six-membered cyclic carbonates from trimethylolpropane and ialkyl carbonates", Green Chemistry, 2011, pp. 976-982, vol. 13.
Sang-Hyun Pyo et al., "Lipase-mediated synthesis of six-membered cyclic carbonates from trimethylolpropane and dialkyl carbonates: Influence of medium engineering on reaction selectivity", Journal of Molecular Catalysis B: Enzymatic, 2011.
Sunggak Kim et al., "Preparation of cyclic carbonates and 2-oxazolidones using di-2-pyridyl carbonate", Heterocycles, 1986, pp. 1625-1630, vol. 24, No. 6.
Dexter B. Pattison, "Cyclic ethers made by pyrolysis of carbonate esters", Journal of the American Chemical Society, 1957, pp. 3455-3456, vol. 79.
Supplemental European Search Report, dated Sep. 25, 2014, from corresponding EP application.

* cited by examiner

*Primary Examiner* — Samantha Shterengarts
*Assistant Examiner* — Matt Mauro
(74) *Attorney, Agent, or Firm* — Young & Thompson

(57) ABSTRACT

Linear or cyclic carbonates as potential monomers for isocyanate-free polyurethanes and polycarbonates were prepared from polyols and dialkyl carbonates or diphenyl carbonates. This invention was developed to produce linear or cyclic carbonates with or without using catalysts. Polyol compounds were reacted with carbonates such as dimethyl carbonate and diethyl carbonate to produce the corresponding linear and/or cyclic carbonate.

13 Claims, 4 Drawing Sheets

METHOD FOR PRODUCING CYCLIC CARBONATES

FIELD OF THE INVENTION

This invention relates to a method of producing cyclic carbonates.

BACKGROUND OF THE INVENTION

With increasing interest in greener alternative processes to produce chemicals and materials, cyclic carbonates, which are potential monomers for the environmentally benign production of aliphatic polycarbonates and polyurethanes by ring-opening polymerization (ROP), have attracted attention in recent years. These aliphatic polymers, besides having traditional applications in engineering, optical devices, seatings, seals, coatings and high performance adhesives, are expected also to find use in biomedical field because of their biocompatibility and low toxicity.

Aliphatic polycarbonates are currently produced industrially from an alkanediol, such as 1,6-hexanediol, and phosgene, triphosgene and dialkyl carbonates. Polyurethanes are produced using polyols, such as alkanediols and glycerol, and isocyanate, which is derived from the reaction between an amine and phosgene. Since phosgene and low-molecular weight isocyanates have undesirable toxicological profiles, attempts have been made to develop routes to make polyurethanes from other sources however none of these have yet been commercially established. A demand has now emerged for isocyanate free polyurethanes for different applications using environmentally friendly production process.

Lately, a number of reports have appeared on the synthesis of cyclic carbonates by a phosgene-free route, but have focused on five-membered cyclic carbonate including addition of carbon dioxide to epoxides using metal containing catalysts under pressure, and by transesterification of polyols with dialkyl carbonate using metal-, or enzymatic (lipase) catalysis. For use in ROP process, however, six-membered cyclic carbonates are preferred to the five-membered one because of being less thermodynamically stable than its ring-opened polymer and thus retaining $CO_2$, during the polymerization process.

Synthesis of six-membered trimethylene carbonate is traditionally achieved by reacting 1,3-propanediol with phosgene or its derivatives. Among the other reactions studied, metal catalysed coupling of oxetane such as trimethylene oxide with carbon dioxide has given high yields of trimethylene carbonate. A method of cyclic carbonate synthesis from 1,3-propanediol and ethyl chloroformate in the presence of a stoichiometric amount of triethylamine has been reported. Transesterification of 1,3-propanediol with dialkyl carbonate catalyzed by metal or organo-catalysts has been proposed as a more environmentally benign procedure. Syntheses of six-membered cyclic carbonates with functional groups from poly-functional alcohol such as trimethylolpropane (TMP) or pentaerythritol (PE) have required more complicated methods with low yields. Polycyclic six-membered carbonates could be prepared by radical polymerization of acrylic monomers with pendant cyclic carbonate groups. As a different approach, tris- or tetrakis (alkoxycarbonyloxy) derivatives, obtained from catalytic transesterification of trimethylolpropane (TMP) and diethyl carbonate (DEC), have been subjected to thermal disproportionation using Aerosil 200 at 200-220° C. followed by distillative depolymerisation under reduced pressure, to give the cyclic product 5-ethyl-5-ethoxycarbonyloxymethyl-1,3-dioxan-2-one with a low yield.

Lipase catalysed synthesis of the six-membered cyclic trimethylene carbonate from 1,3-diol and dimethyl or diethyl carbonate has been achieved in a solvent system of acetonitrile and toluene (4:1, v/v) using very high concentration (600-900% w/w of the diol) of the immobilized *Candida antarctica* lipase B, Novozym®435 (N435), however with moderate yield (53%) and low productivity.

Synthesis of cyclic carbonates with functional groups using lipase-mediated reaction between TMP and dialkyl carbonate in solvent free condition has recently been reported. The product formed was a mixture of cyclic- and linear (mono-, di- and tri-) carbonates, the proportions of which depended on the reaction conditions used. Subjecting the product mixture to thermal cyclization at 70-90° C. without the biocatalyst converted the linear carbonates to the cyclic ones. However these enzymatic reactions have limitation of high enzyme cost.

SUMMARY OF THE INVENTION

The present invention aims to provide a facile, green and cost effective production method with or without using catalysts such as metal catalysts. The method disclosed herein may be performed without intermediate isolation steps.

In one aspect the present invention relates to a method of producing linear or cyclic carbonates comprising the steps of:
 a. providing a polyol and a dialkyl carbonate or a diphenyl carbonate
 b. forming a mixture of a polyol and a dialkyl carbonate or a diphenyl carbonate;
 c. optionally adding a solvent;
 d. optionally adding an adsorbent; and
 e. heating the mixture to obtain linear or cyclic carbonates;
wherein no catalyst is used.

In a second aspect the present invention relates to a method of producing linear or cyclic carbonates comprising the steps of:
 a. providing a polyol and a dialkyl carbonate or a diphenyl carbonate
 b. forming a mixture of a polyol and a dialkyl carbonate or a diphenyl carbonate;
 c. optionally adding a solvent;
 d. optionally adding an adsorbent; and
 e. heating the mixture to obtain linear or cyclic carbonates.

Specific embodiments of the present inventions are found in the dependent claims.

BRIEF DESCRIPTION OF THE FIGURES

A more complete appreciation of the invention, and many of the attendant advantages thereof, will be readily apparent and better understood by reference to the following detailed description and figures.

In FIG. 1:

R=alkyl, phenyl

R1, R2, R3, R4, R5, R6=H, alkyl, hydroxyl, hydroxyalkyl, alkylcarbonyl, carbonylalkyl, alkoxycarbonyl, alkoxycarbonyloxy and carboxyl group, independently.

Figure 2:
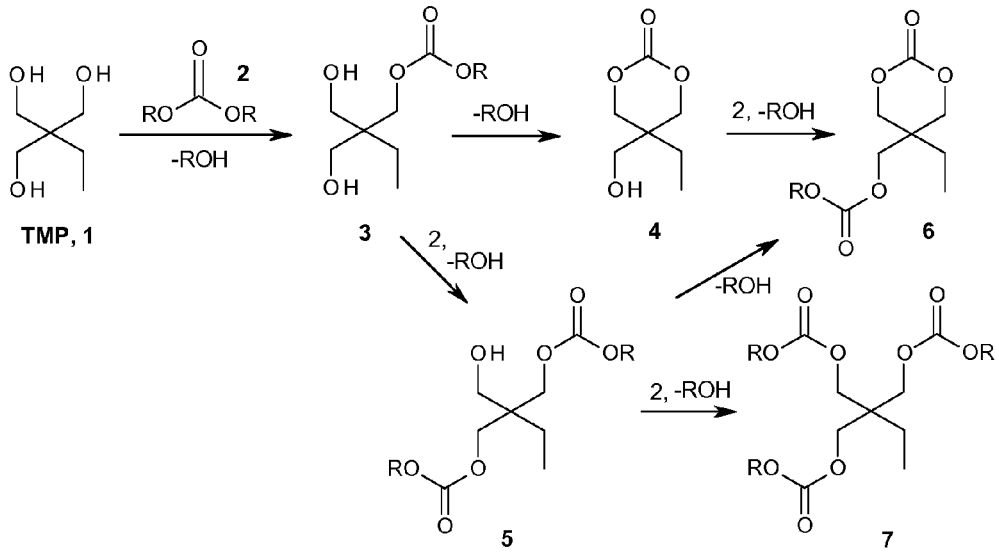

FIG. 2. Reaction of TMP with dimethyl carbonate.

Figure 3:
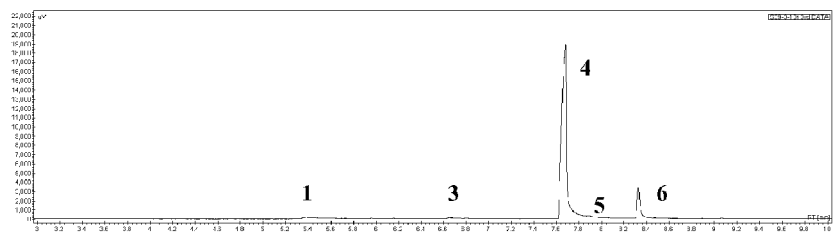

FIG. 3. Representative GC chromatogram (Run 9, Table 5).

Figure 4:
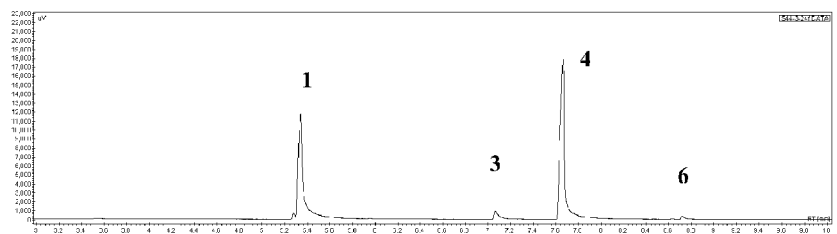

FIG. 4. Representative GC chromatogram (Run 16, Table 5).

Figure 5:
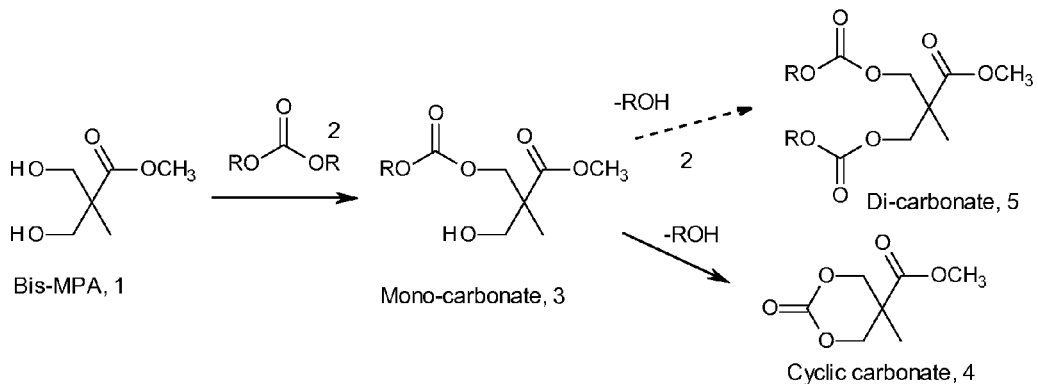

FIG. 5. Reaction of Bis-MPA methylester with dialkyl carbonate.

Figure 6:
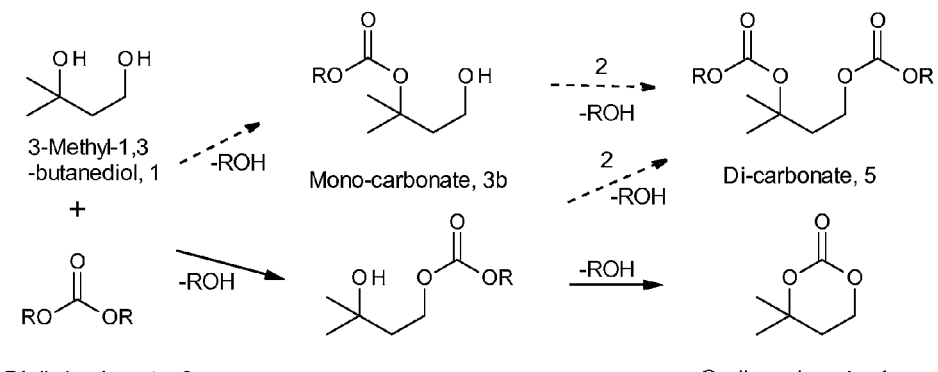

FIG. 6. Reaction of 3-methyl-1,3-butanediol with DMC.

Figure 7:
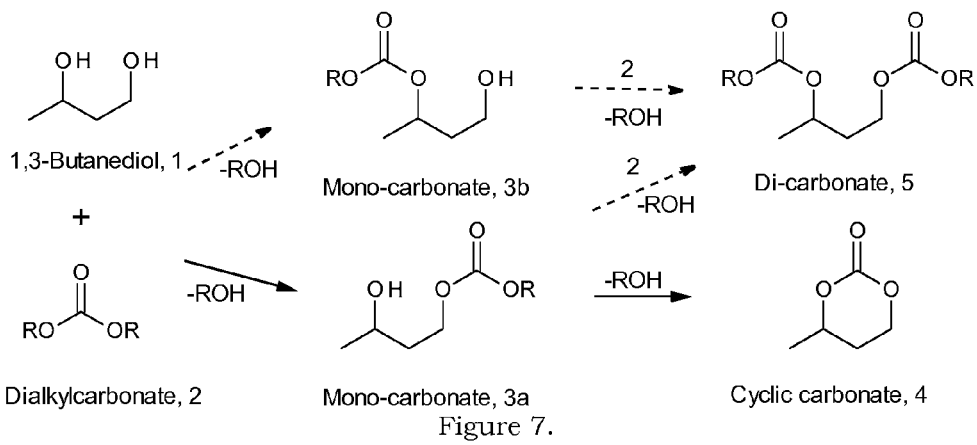

FIG. 7. Reaction of 1,3-butanediol with DMC.

Figure 8:
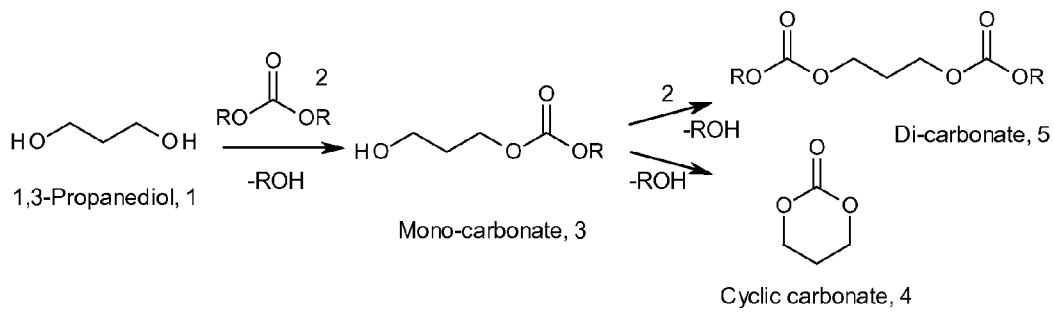

FIG. 8. Reaction of 1,3-propanediol with DMC.

Figure 9:
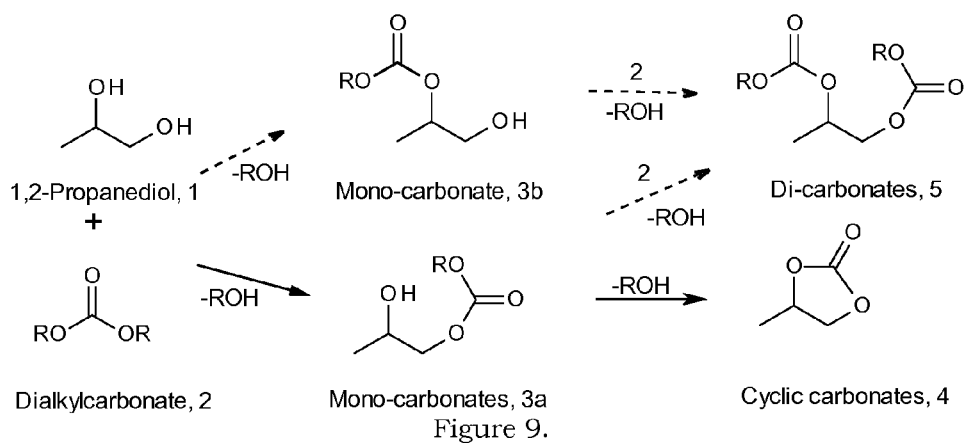

FIG. 9. Reaction of 1,2-propanediol with DMC.

Figure 10:
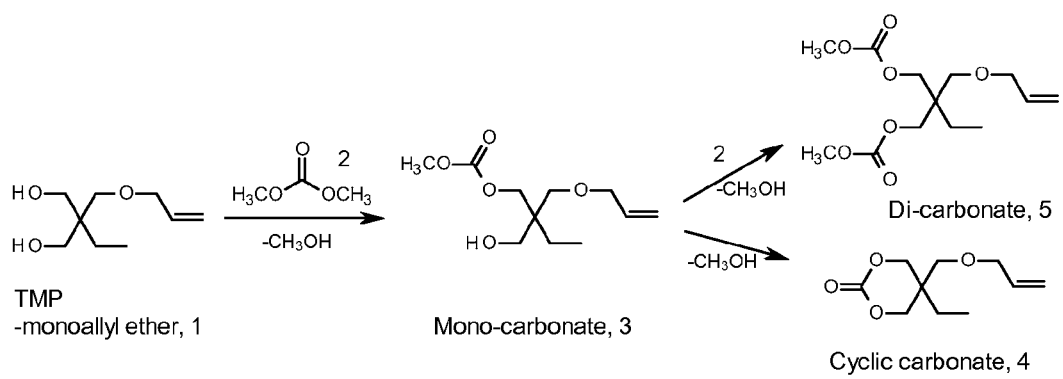

FIG. 10. Schematic reaction of TMP-monoallyl ether with DMC.

Figure 11:
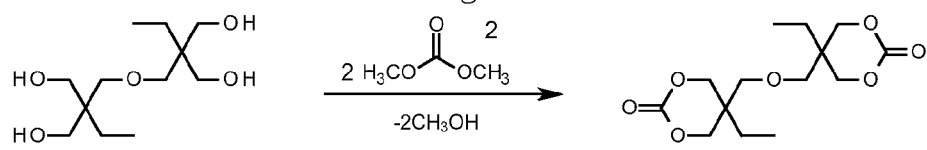

FIG. 11. Schematic reaction of di-trimethylolpropane with DMC.

Figure 12:
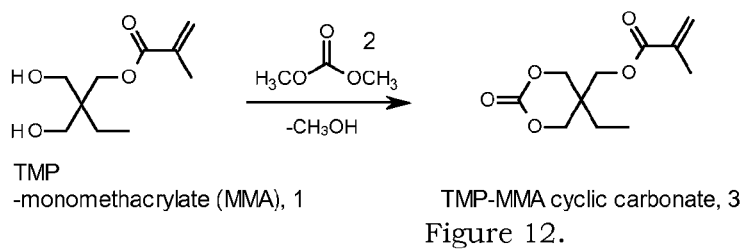

FIG. 12. Schematic reaction of TMP-monomethacrylate with DMC.

DETAILED DESCRIPTION OF THE INVENTION

In the present invention the word "substrate" means a polyol if nothing else is stated.

The aim of the present invention is to provide a novel and inventive method for producing linear and/or cyclic carbonates that is both environmentally friendly, inexpensive and does not require isolating steps.

In general, the method according to the present invention uses dialkyl carbonates or diphenyl carbonates as one of the reactants and together with a polyol and they may form linear and/or cyclic structures preferably by the use of adsorbents and heating. The present invention presents a method that discloses a very high yield even without using catalysts such as metals or enzymes. Additionally, unlike prior art there is also no need for an isolation step where solids and catalyst are removed. In other words the present invention discloses a single step method that does not need to use a catalyst in order to obtain high yield. This is in particular very interesting for forming cyclic carbonates.

A further advantage of the present invention is the high selectivity of the formed products. As is further disclosed in the examples, very high selectivity can be reached by using the method of the present invention, both for linear and cyclic products. As is disclosed in the examples the use of an adsorbent increases the selectivity of the formed product. Without being bound by theory, it is believed that the adsorption of formed alcohol minimizes the risk of side reactions caused by the alcohol.

The present invention further discloses a method wherein an increase in the temperature above the reflux temperature, the boiling temperature, of the carbonate used will dramatically increase the yield of the obtained product. Even without the use of molecular sieves the formation of cyclic carbonates discloses high yields.

For linear or cyclic carbonate formation, the general method comprises reacting a polyol compound with a carbonate such as dialkyl carbonate for example dimethyl carbonate or diethyl carbonate, or diphenyl carbonate to produce a corresponding linear and/or cyclic carbonate preferably by heating with or without the use of an adsorbent such as molecular sieves. This leads to an increased product selectivity and/or yield. The proportion of cyclic carbonate can be improved from the remaining linear carbonates in the mixture by thermal cyclization with or without molecular sieves. The resulting cyclic carbonates can be used to produce isocyanate-free polymers.

Furthermore, polymers containing reactive functional groups such as alkyl, allyl, phenyl, hydroxyl, allyl alkyl, allyl ether and carboxylic acid, which can be used to modify the properties, can be provided. Even greater diversity of cyclic carbonate and their polymers can be achieved by preparation and employment of various 5-, 6-, 7- and higher membered cyclic carbonates. The inventors have recently investigated the synthesis of for example six-membered cyclic carbonates (—O—CO—O—) with functional groups using lipase-mediated reaction between TMP and dialkyl carbonate.

Another embodiment of the present invention relates to thermal cyclization of linear carbonates without any catalyst.

Cyclic Carbonate Formation Reaction.

Figure 1:
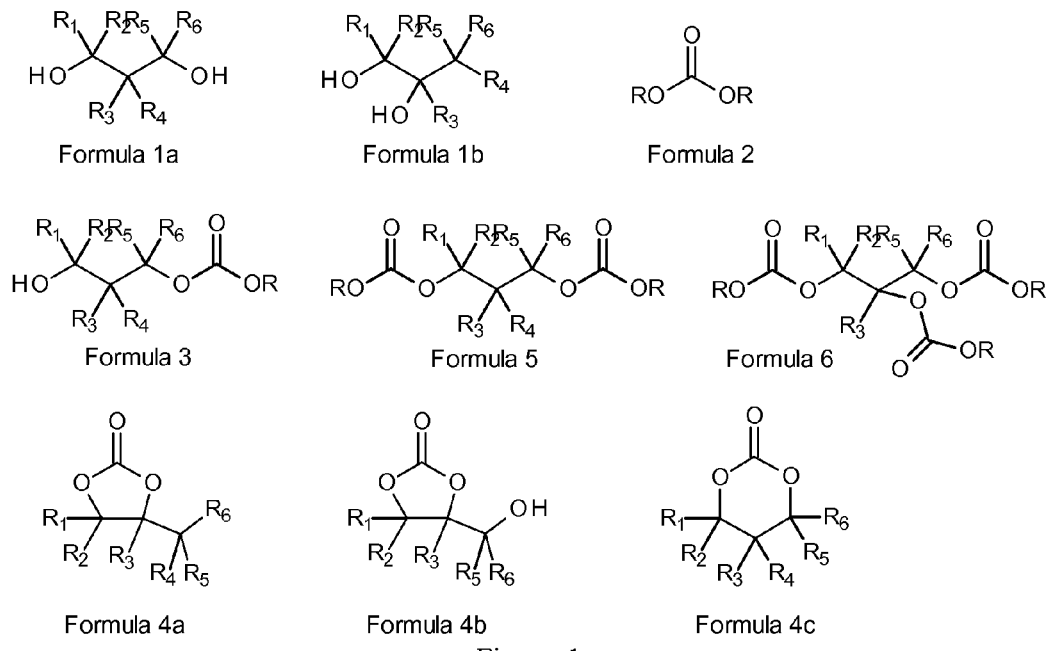
FIG. 1. General formulae of reactants and products of the present invention for the formation of cyclic carbonates. Polyol compounds (formula 1) react with dialkyl- or diphenyl-carbonate (formula 2) to give cyclic carbonate (for example: formula 4a, 4b and 4c) and/or linear carbonates (for example: formula 3, 5 and 6).

FIG. 1 discloses general compounds that may be used for the formation of cyclic carbonates according to the present invention. A polyol compound (Formula 1) is reacted with a dialkyl or diphenyl carbonate (Formula 2) preferably during heating in the absence or presence of a catalyst. An organic is not necessary for the reaction but can be used. An adsorbent, preferably a solid phase adsorbent, for example molecular sieves can be used in the reaction to remove the resulting by-product such as methanol or ethanol. But the function of molecular sieves is not limited to absorb the resulting alcohol. Without being bound by theory but it is believed that a higher selectivity of cyclic carbonates can be obtained by using an adsorbent such as molecular sieves.

The ratio of used catalyst, adsorbent and dialkyl carbonates or diphenyl carbonates to polyols is not limited. The catalyst can preferably be used at a ratio to the polyol of 1 to 200 wt % preferably 1 wt % or more, or 10 wt % or more, or 30 wt % or more, or 50 wt % or more, or 80 wt % or more, or 100 wt % or more, or 200 wt % or less, or 180 wt % or less, or 150 wt % or less, or 120 wt % or less, such as 1, 10, 50, 70, 100, 150 and 200 wt %.

The adsorbent can preferably be used at a ratio to the polyol of 10 to 2000 wt % preferably 10 wt % or more, or 50 wt % or more, or 100 wt % or more, or 200 wt % or more, or 300 wt %, or 500 wt % or more, or 750 wt % or more, or 1000 wt % or more, or 2000 wt % or more, or 1700 wt % or more, or 1500 wt % or more, or 1200 wt % or more, such as 10, 100, 200, 300, 500, 700, 1000, 1500 and 2000 wt %. A preferred range is 100 to 600 wt %, in one embodiment the range is 150 to 350 wt %.

The dialkyl carbonate or the diphenyl carbonate can preferably be used at a ratio to the polyol of 0.1 to 3000 wt % preferably 100 wt % or more, or 150 wt % or more, or 200 wt % or more, or 500 wt % or more, or 1000 wt % or more, or 1500 wt % or more, or 3000 wt % or less, or 2500 wt % or less, or 2000 wt % or less, or 1700 wt % or less, such as 100, 300, 700, 1000, 1500, 2000, 2500 and 3000 wt %, respectively. In one embodiment the polyol:dialkyl carbonate or diphenyl carbonate weight ratio is from 1:10 to 600:1 such as 1:10 or more, or 3:10 or more, or 7:10 or more, or 1:1 or more, or 2:1 or more, or 4:1 or more, or 5:1 or more, 7:1 or more, or 10:1 or more, 20:1 or more, or 25:1 or more, or 30:1 or more, or 40:1 or more, or 600:1 or less, or 500:1 or less, or 300:1 or less, or 200:1 or less, 100:1 or less, or 80:1 or less, or 60:1 or less, or 55:1 or less, or 45:1 or less. A preferred range is 25:1 to 50:1 or even more preferred 30:1 to 40:1.

The method according to the invention comprises the steps of:

a. providing a polyol and a dialkyl carbonate or a diphenyl carbonate
b. forming a mixture of a polyol and a dialkyl carbonate or a diphenyl carbonate;
c. optionally adding a solvent;
d. optionally adding an adsorbent; and
e. heating the mixture to obtain linear or cyclic carbonates;

wherein no catalyst is used.

If the reaction is performed without an adsorbent such as molecular sieves then preferably a catalyst is used. Also, the conversion rate increases with increase in temperature and preferably the temperature should be more than 80° C., such as 90° C. or more or 100° C. or more or 120° C. or more. Preferred catalysts are metal catalysts, more preferred catalysts are silica, $Bi_2O_3$, BaCO3, RbCl, $FeCl_3.6H_2O$, $CoCl_2.6H_2O$, $SnCl_2$, $CaCO_3$, $MnCl_2$, NaOH or $Na_2CO_3$ or combinations thereof. Even more preferred catalysts are RbCl, $Na_2CO_3$ and $Bi_2O_3$ or combinations thereof.

When using an adsorbent such as molecular sieves during the reaction no catalyst is needed, and in one embodiment the absence of a catalyst such as lipase is preferred. In order to obtain a high yield of the cyclic carbonate a high reaction temperature is preferred. The temperature should preferably be at the boiling point of the carbonate used. As a non limited example the temperature could be 80° C. or more, such as 90° C. or more or 100° C. or more or 120° C. or more, or 140° C. or more. The amount of molecular sieves, or adsorbent, is believed to influence the reaction time, i.e. more the molecular sieves the faster the reaction will be. This is probably only true up to a certain amount of adsorbent. In a preferred embodiment of the present invention the weight ratio of adsorbent to substrate (polyols), should preferably be from 0.1:1 to 20:1, i.e. 0.1:1 or more, or 1:1 or more or 2:1 or more, or 4:1 or more, or 6:1 or more, or 8:1 or more, or 20:1 or less, or 18:1 or less, or 15:1 or less, or 12:1 or less, or 10:1 or less. In another embodiment no adsorbent is used. When no adsorbent is used the temperature is preferably higher than the boiling point of the carbonate, for DMC (dimethyl carbonate) for example the temperature should preferably be more than 100° C., or even more preferred more than 120° C. When DEC, diethyl carbonate, is used the temperature should preferably be 120° C. or more, preferably 140° C.

The adsorbent should preferably be able to adsorb alcohols such as methanol, ethanol or phenol. In a preferred embodiment the adsorbent is a solid phase adsorbent. For example any type of molecular sieve may be used but preferably molecular sieves of the type 3A, 4A or 5A, or most preferred 3A or 4A. The sieves can be in the form of powder, beads or pellets or any other suitable form but preferably beads or pellets.

The method of the present invention could be performed in a closed system creating a pressure increase when heating above the boiling or reflux point.

Further, the reaction may be performed in solution and any organic solvent may be used. However, preferred solvents are THF, toluene, acetonitrile, t-butanol and pyridine or mixtures of the same or mixtures containing said solvents. In one embodiment no additional solvent is added besides the reactants of the process. In one embodiment the amount of solvent is less than 200 wt %, or less than 100 wt %, or less than 75 wt %, or less than 50 wt %, or less than 25 wt %.

The method may be performed using any dialkyl or diphenyl carbonate together with any polyol. The polyol could be a $C_2$ to $C_{15}$ or higher, tetraol, triol or diol or a $C_2$ to $C_{15}$ or higher tetraol, triol or diol alkyl ester or derivatives thereof. The polyol could for example be a $C_2$ to $C_{35}$ or $C_2$ to $C_{15}$. Preferably the polyol is a $C_2$, $C_3$ $C_4$, $C_6$, $C_6$, $C_7$, $C_8$, $C_9$, $C_{10}$, $C_{11}$ or a $C_{12}$ tetraol, triol or diol, or diol alkyl ester or derivatives thereof. In one embodiment the polyol is at least a diol. In another embodiment the polyol is at least a triol. For example bis-MPA methyl ester, trimethylolpropane (TMP), di-trimethylolpropane (Di-TMP), pentaerythritol, TMP-monoallylether (TMP-ME), TMP-monoacrylate (TMP-MA), TMP-monomethacrylate (TMP-MMA), 1,4-butane diol, 1,3-butane diol, 1,2-propane diol and 1,3-propane diol and derivatives thereof such as 3-methyl-1,3-butanediol are all preferred polyols. The alkyl groups of the dialkyl carbonate could have any number of carbons but preferably the alkyl groups are methyl, ethyl, propyl or butyl and isomers thereof. In a preferred embodiment the dialkyl carbonate is dimethyl carbonate or diethyl carbonate.

FIGS. 2 and 5 to 12 disclose different reaction schemes of the present invention using different polyols.

In a preferred embodiment the dialkyl carbonate is dimethyl carbonate or diethyl carbonate, the temperature is 120° C. or more and the weight ratio of adsorbent to substrate is 4:1 or more and the adsorbent is molecular sieves.

Linear monocarbonates may form cyclic carbonates through thermal treatment with or without molecular sieves. This could be performed after step e in the method described above. By heating a mixture containing linear monocarbonates, preferably without any dialkyl or diphenyl carbonate, a high yield of cyclic carbonate may be obtained. Preferably the amount of dialkyl or diphenyl carbonate should be less than 20 wt %, or more preferably less than 10 wt % or even more preferably less than 1 wt % before the thermal treatment starts. Any organic solvents can be used in the thermal treatment. However, preferred solvents are THF, toluene, acetonitrile, t-butanol and pyridine or mixtures of the same or mixtures containing said solvents.

Any solvent is also preferably removed and should be less than 20 wt %, or more preferably less than 10 wt % or even more preferably less than 1 wt % before the thermal treatment starts. The temperature should preferably be at least 80° C., such as 90° C. or more, or 100° C. or more, or 120° C. or more, or 140° C. or more. Any dialkyl or diphenyl carbonate or solvent could be removed by any technique known to a person skilled in the art, for example distillation or evaporation.

Quantitative Analyses and Structure Elucidation

Quantitative analyses of reaction components were performed using gas chromatography (GC, Varian 430-GC, Varian, USA) equipped with FactorFour Capillary column, VF-1 ms (Varian, 15M×0.25 mm) and a flame ionization detector. The initial column oven temperature was increased from 50 to 250° C. at a rate of 20° C./min. After removing the solid portion by centrifugation or filtration, the samples diluted with acetonitrile to a final concentration of 0.1-0.5 mg/mL, were injected in split injection mode of 10% at 275° C. The conversion of substrates and ratio of products were calculated by comparison of peak areas on the gas chromatograms.

The structures of the products were then determined by 1H-NMR using 400 MHz NMR (Bruker, UltraShield Plus 400, Germany) and comparison with literature.

The product could be separated by general techniques such as distillation, liquid-liquid extraction, precipitation and crystallization.

EXAMPLES

The present invention is further explained in more detail with reference to the following examples. These examples, however, should not be interpreted as limiting the scope of the present invention in any manner.

Example 1

Reaction of TMP with Dimethyl Carbonate

FIG. 3 discloses the reaction of TMP with DMC. 50 mg TMP (1) was dissolved in 1.5 mL DMC in a 4 mL vial, and reacted by heating at 100° C. with 25 mg catalyst using Thermomixer. Small aliquots of reaction samples were taken for analysis at varying time intervals. Table 1 shows the composition of the product mixture at a defined time.

TABLE 1

| Run | Catalyst | Time (h) | Start. (1) | 3 | Products (%) 4 (Sel)[a] | 5 | 6 |
|---|---|---|---|---|---|---|---|
| 1 | Silica | 24 | 95.1 | 2.2 | 2.8 (57.1) | 0 | 0 |
| 2 | Bi$_2$O$_3$ | 24 | 7.5 | 17.5 | 45.8 (49.5) | 12.5 | 15.9 |
| 3 | BaCO$_3$ | 24 | 87.5 | 7.3 | 5.2 (41.6) | 0 | 0 |
| 4 | RbCl | 12 | 1.4 | 5.7 | 65.2 (66.1) | 6.3 | 21.3 |
| 5 | Na$_2$CO$_3$ | 12 | 0 | 3.8 | 19.5 (19.5) | 23.4 | 43.4 |
| 6 | FeCl$_3$·6H$_2$O | 12 | 19.2 | 39.5 | 31 (38.4) | 15.1 | 5.3 |
| 7 | CoCl$_2$·6H$_2$O | 24 | 92.4 | 6.3 | 1.3 (17.1) | 0 | 0 |
| 8 | SnCl$_2$ | 24 | 70.7 | 15.7 | 13.6 (46.4) | 0 | 0 |
| 9 | CaCO$_3$ | 24 | 91.7 | 5.9 | 2.4 (28.9) | 0 | 0 |
| 10 | MnCl$_2$ | 24 | 74.8 | 18.5 | 6.7 (26.6) | 0 | 0 |
| 11[b] | Na$_2$CO$_3$ | 24 | 50.4 | 15.4 | 28.2 (56.9) | 4.5 | 1.6 |

[a](Sel): Percent of the total product amount (3, 4, 5 and 6).
[b]100 mg TMP, 3 mL DMC, 10 mg Na$_2$CO$_3$, and 80° C. reaction temperature.

$^1$H-NMR(CDCl$_3$)

Product 4. 0.956 (3H, t), 1.533 (2H, q), 3.715 (2H, s), 4.172 (2H, d), 4.348 (2H, d).

Example 2

Reaction of TMP with Dimethyl Carbonate 50 mg TMP (1) was dissolved in 1.5 mL DMC in a 4 mL vial, and reacted by heating at 100° C. with 25 mg catalyst and 0.2 g molecular sieves (4 Å, bead type) using Thermomixer. Small aliquots of reaction samples were taken for analysis at varying time intervals. Table 2 shows the product compositions after 24 h reaction with different catalysts.

TABLE 2

| Run | Catalyst | Time (h) | Start. (1) | 3 | Products (%) 4 (Sel)[a] | 5 | 6 |
|---|---|---|---|---|---|---|---|
| 1 | Silica | 24 | 75.8 | 3.7 | 20.4 (84.3) | 0 | 0 |
| 2 | Bi$_2$O$_3$ | 24 | 66.7 | 4.8 | 28.0 (84.2) | 0 | 0.7 |
| 3 | BaCO$_3$ | 24 | 63 | 4.6 | 30.6 (82.7) | 1 | 0.8 |
| 4 | RbCl | 24 | 56.7 | 4.2 | 38.5 (88.9) | 0 | 0.6 |
| 5 | Na$_2$CO$_3$ | 24 | 4.7 | 6.8 | 69.1 (72.5) | 5.1 | 14.3 |
| 6 | FeCl$_3$·6H$_2$O | 24 | 74.9 | 3 | 22.2 (88.4) | 0 | 0 |
| 7 | CoCl$_2$·6H$_2$O | 24 | 87.3 | 4.3 | 8.5 (66.9) | 0 | 0 |
| 8 | SnCl$_2$ | 24 | 76.9 | 4.7 | 17.1 (74.0) | 0.7 | 0.7 |
| 9 | CaCO$_3$ | 24 | 65.9 | 4.9 | 27.7 (81.2) | 1.1 | 0.4 |
| 10 | MnCl$_2$ | 24 | 79.7 | 12.2 | 8.1 (39.9) | 0 | 0 |
| 11 | TiO$_2$ | 24 | 84.4 | 3.6 | 12.0 (76.9) | 0 | 0 |
| 12 | MgSO$_4$ | 24 | 66.3 | 3.3 | 29.9 (88.7) | 0 | 0 |
| 13[b] | Na$_2$CO$_3$ | 24 | 55.9 | 3.7 | 37.4 (84.8) | 2.2 | 0.6 |

[a](Sel): Percent of the total product amount (3, 4, 5 and 6).
[b]100 mg TMP, 3 mL DMC, 10 mg Na$_2$CO$_3$, and 80° C. reaction temperature.

Example 3

Reaction of TMP with Dimethyl Carbonate

TMP (1) was dissolved in DMC in 4 or 20 mL vial, and reacted by heating with different types of molecular sieves (MS) using Thermomixer or in oil bath. Small aliquots of reaction samples were taken for analysis at varying time intervals. Table 3 shows the product composition of the reactions at defined time intervals in the presence of molecular sieves of different grades.

TABLE 3

| Run | MS (g) | TMP (mg) | DMC (mL) | Temp (C.) | Time (h) | Start (1) | 3 | Products (%) 4 (Sel)[a] | 5 | 6 |
|---|---|---|---|---|---|---|---|---|---|---|
| 1 | 0 | 50 | 1.5 | 100 | 24 | 39 | 19.6 | 34.7 (56.9) | 3.8 | 2.8 |
| 2 | 0.2 (4A, Bead) | 50 | 1.5 | 100 | 24 | 66.6 | 2.8 | 29.9 (89.5) | 0.7 | 0 |
| 3 | 0.6 (3A, Bead) | 100 | 3 | 120 | 15 | 18.3 | 2.4 | 72 (88.1) | 1.6 | 5.7 |
| 4 | 0.6 (4A, Bead) | 100 | 3 | 120 | 24 | 23.1 | 1.1 | 72 (93.6) | 0.3 | 3.5 |
| 5 | 0.6 (3A, Pellet) | 100 | 3 | 120 | 6 | 11.2 | 6.7 | 71.9 (81.0) | 2.7 | 7.5 |

[a](Sel): Percent of the total product amount (3, 4, 5 and 6).

Example 4

Reaction of TMP with Dimethyl Carbonate 50 mg TMP (1) was dissolved in 0.25 mL DMC and 1 mL solvent in a 4 mL vial, and reacted by heating at 100° C. with 0.2 g molecular sieves (4 Å, bead type) using Thermomixer. Small aliquots of reaction samples were taken for analysis at varying time intervals. Table 4 gives the product composition after 24 h reaction in different solvents.

TABLE 4

| Run | Solvent (1 mL) | TMP (mg) | DMC (mL) | Time (h) | Starting (1) | 3 | 4 (Sel)[a] | 5 | 6 |
|---|---|---|---|---|---|---|---|---|---|
| 1 | t-Butanol | 50 | 0.25 | 24 | 91.3 | 1 | 7.7 (88.5) | 0 | 0 |
| 2 | Acetonitrile | 50 | 0.25 | 24 | 26.8 | 4.2 | 65 (88.8) | 2.2 | 1.8 |
| 3 | Pyridine | 50 | 0.25 | 24 | 0 | 6.9 | 47.7 (47.7) | 11.4 | 24.3 |

[a](Sel): Percent of the total product amount (3, 4, 5 and 6).

Example 5

Reaction of TMP with Dialkyl Carbonate or Diphenyl Carbonate

TMP (1) was dissolved in DMC or DEC (2) (or diphenyl carbonate, run 17) in 4 or 20 mL vial, and reacted by heating with molecular sieves (MS) 4 Å using Thermomixer or in oil bath (Table 5). Small aliquots of reaction samples were taken for analysis at varying time intervals. FIGS. 3 and 4 disclose the GC chromatogram from run 9 and run 16. Table 5 shows the results after defined time intervals of the reactions performed under different conditions.

TABLE 5

| Run | TMP (mg) | DMC (mL) | MS (g) | Temp. (° C.) | Time (h) | Starting (1) | 3 | 4 (Sel)[a] | 5 | 6 |
|---|---|---|---|---|---|---|---|---|---|---|
| 1 | 50 | 1.5 | 0 | 80 | 24 | 99.1 | 0.9 | 0 (0) | 0 | 0 |
| 2 | 50 | 1.5 | 0.2 | 80 | 24 | 87.2 | 4.9 | 7.9 (61.7) | 0 | 0 |
| 3 | 200 | 6 | 0 | reflux | 24 | 100 | 0 | 0 (0) | 0 | 0 |
| 4 | 200 | 6 | 1.2 | reflux | 24 | 84.3 | 3.5 | 11.5 (73.3) | 0.8 | 0 |
| 5 | 50 | 1.5 | 0.2 | 100 | 24 | 40.5 | 2.5 | 54.3 (91.3) | 1.3 | 1.4 |
| 6 | 50 | 1.5 | 0.2 | 100 | 96 | 3.3 | 2.1 | 86 (88.9) | 0.8 | 7.8 |
| 7 | 100 | 3 | 0 | 120 | 12 | 9.9 | 25.6 | 43.2 (47.9) | 11.6 | 9.6 |
| 8 | 100 | 3 | 0.3 | 120 | 12 | 34.2 | 3.3 | 60.4 (91.8) | 0.9 | 1.3 |
| 9 | 100 | 3 | 0.6 | 120 | 13 | 1.5 | 0 | 89.0 (90.4) | 0.7 | 8.8 |
| 10 | 100 | 3 | 0.9 | 120 | 12 | 4.6 | 1.7 | 82.7 (86.7) | 2.3 | 8.9 |
| 11 | 200 | 6 | 1.2 | 120 | 4 | 30.4 | 3.9 | 62.5 (89.8) | 2.5 | 0.7 |
| 12 | 200 | 6 | 1.2 | 120 | 14 | 0 | 0 | 88.3 (88.3) | 10.6 | 1.2 |
| 13 | 100 | 3 | 0.6 | 140 | 1 | 4.7 | 6 | 75.6 (79.3) | 3.3 | 10.4 |
| 14 | 100 | 3 | 0.6 | 140 | 2 | 0.6 | 3.2 | 73.5 (73.9) | 4.1 | 18.6 |
| 15[b] | 100 | 3 (DEC) | 0.6 | 120 | 12 | 87.7 | 3.1 | 9.3 (75.6) | 0 | 0 |
| 16[b] | 100 | 3 (DEC) | 0.6 | 140 | 24 | 41.9 | 2.6 | 54.9 (94.5) | 0.6 | 0 |
| 17[c] | 50 | 1 (DPC) | 0 | 110 | 4 | 0 | 0 | 41.5 | 0.0 | 0 |

[a](Sel): Percent of 4 in the products.
[b]DEC was used as the dialkyl carbonate.
[c]Diphenyl carbonate (DPC) was used. 58.5% by-products.

Example 6

Reaction of Bis-MPA Methylester with Dialkyl Carbonate

FIG. 5, Bis-MPA methyl ester (1, MPA) was dissolved in DMC (2) in 4 or 20 mL vial, and reacted by heating with molecular sieves 4A using Thermomixer or in oil bath. Small aliquots of reaction samples were taken for analysis at varying time intervals and Table 6 summarises the results.

TABLE 6

| Run | MPA (mg) | DMC (mL) | Molecular sieves (g) | Temp. (° C.) | Time (h) | Starting (1) | 3 | 4 (Sel)[a] | 5 |
|---|---|---|---|---|---|---|---|---|---|
| 1 | 50 | 1.5 | 0.2 | 100 | 48 | 58.5 | 17 | 23.4 (56.4) | 1.1 |
| 2 | 50 | 1.5 | 0.2 | 100 | 72 | 46.4 | 18.3 | 33.5 (62.5) | 1.8 |
| 3 | 100 | 3 | 0.6 | 120 | 48 | 10.1 | 15.6 | 67 (74.5) | 7.3 |
| 4 | 100 | 3 | 0.6 | 120 | 72 | 0 | 12.8 | 73.3 (73.3) | 13.9 |
| 5 | 100 | 3 | 0.6 | 140 | 8 | 17.2 | 24.1 | 52.5 (63.4) | 6.1 |
| 6 | 100 | 3 | 0.6 | 140 | 24 | 0 | 17 | 62 (62.0) | 21 |
| 7[b] | 100 | 3 (DEC) | 0.6 | 140 | 24 | 70.5 | 24.4 | 5.1 (17.3) | 0 |

[a](Sel); selectivity of 4 in the products.
[b]DEC was used as the dialkyl carbonate.

¹H-NMR(CDCl₃)

Product 4. 1.275 (3H, s), 3.758 (3H, s), 4.324 (4H, m)

Example 7

Reaction of 3-methyl-1,3-butanediol with DMC

FIG. 6, 3-Methyl-1,3-butanediol (1, 3M13BD) was dissolved in DMC (2) in a 20 mL vial, and reacted by heating at 120° C. with molecular sieves 4A in oil bath. Small aliquots of reaction samples were taken for analysis at varying time intervals. Table 7 shows the results after 7 and 24 hours of reaction.

TABLE 7

| Run | 3M13BD (mg) | DMC (mL) | Molecular sieves (g) | Temp. (° C.) | Time (h) | Starting (1) | Products (%) 3a, b | 4 (Sel)ᵃ | 5 |
|---|---|---|---|---|---|---|---|---|---|
| 1 | 100 | 3 | 0.6 | 120 | 7 | 41.2 | 47.6 | 11.2 (19.5) | 0 |
| 2 | 100 | 3 | 0.6 | 120 | 24 | 0 | 26.8 | 71.6 (71.6) | 1.9 |

ᵃ(Sel); selectivity of 4 in the products.

¹H-NMR(CDCl₃)

Product 4. 1.507 (6H, s), 2.022 (2H, t), 4.451 (2H, t)

Example 8

Reaction of 1,3-butanediol with DMC

FIG. 7, 1,3-Butanediol (1; 1,3BD) was dissolved in DMC (2) in a 20 mL vial, and reacted by heating with molecular sieves 4A in oil bath. Small aliquots of reaction samples were taken for analysis at varying time intervals. Table 8 summarises the product composition after different reaction time intervals.

TABLE 8

| Run | 1,3BD (mg) | DMC (mL) | Molecular sieves (g) | Temp. (° C.) | Time (h) | Starting (1) | Products (%) 3 | 4 (Sel)ᵃ | 5 |
|---|---|---|---|---|---|---|---|---|---|
| 1 | 100 | 3 | 0.6 | 120 | 7 | 10.9 | 28 | 54.9 (60.6) | 6.1 |
| 2 | 100 | 3 | 0.6 | 120 | 18 | 0 | 16.8 | 30.5 (30.5) | 52.7 |

ᵃ(Sel). Percent of the total product amount (3, 4, and 5).

¹H-NMR(CDCl₃)

Product 4. 1.346 (3H, d), 1.989 (2H, m), 4.221 (2H, b), 4.902 (1H, b).

Example 9

Reaction of 1,3-propanediol with DMC

FIG. 8, 1,3-propanediol (1, 13PD) was dissolved in DMC (2) in a 20 mL vial, and reacted in the presence of molecular sieves 4A by heating in oil bath. Small aliquots of reaction samples were taken for analysis at varying time intervals. Table 9 shows the results after 1 and 7 hours of the reaction.

TABLE 9

| Run | 13PD (mg) | DMC (mL) | Molecular sieves (g) | Temp. (° C.) | Time (h) | Starting (1) | Products (%) 3 | 4 | 5 |
|---|---|---|---|---|---|---|---|---|---|
| 1 | 100 | 3 | 0.6 | 120 | 1 | 0 | 46.3 | 7.6 | 46 |
| 2 | 100 | 3 | 0.6 | 120 | 7 | 0 | 0 | 0 | 100 |

Example 10

Reaction of 1,2-propanediol with DMC

FIG. 9, 1,2-propanediol (1; 1,2PD) was dissolved in DMC (2) in a 20 mL vial, and reacted by heating with molecular sieves 4A (0.6 g) in oil bath. Small aliquots of reaction samples were taken for analysis at varying time intervals. Table 10 shows the results after 1 and 7 hours of reaction.

TABLE 10

| Run | 12PD (mg) | DMC (mL) | Temp. (° C.) | Time (h) | Starting (1) | Products (%) 3 | 4 | 5 |
|---|---|---|---|---|---|---|---|---|
| 1 | 100 | 3 | 120 | 1 | 77.6 | 0 | 22.4 | 0 |
| 2 | 100 | 3 | 120 | 7 | 0 | 0 | 100 | 0 |

¹H-NMR(CDCl₃)

Product 4. 1.508 (3H, d), 4.047 (1H, t), 4.572 (2H, t), 4.875 (1H, m).

Example 11

Thermal Cyclization of Mono-Carbonates Resulting from Reaction of 3-Methyl-1,3-butanediol with DMC The yield of cyclic carbonate can be improved by thermal cyclization of mono-carbonates without using any catalyst. 200 mg 3-Methyl-1,3-butanol was reacted with dimethyl carbonate at 120° C. for 24 h. Resulting product mixture was recovered by centrifugation or filtration to remove solid materials, and followed by evaporation of excess dialkyl carbonate. The recovered product mixture was shaken on Thermomixer. At 80° C., product 3a was converted to cyclic carbonate (4) by heating for 24 h, but the amount of 3b was unchanged (Table 11, Run 2). However, product 3b was converted by additional reaction at 90° C. for 24 h (Table 11, Run 3).

TABLE 11

| Run | Temp. (° C.) | Time (h) | Starting (1) | 3a | 3b | 4 | 5 |
|---|---|---|---|---|---|---|---|
| 1 |  | 0 | 0 | 15.6 | 19 | 63.4 | 2.1 |
| 2 | 80 | 24 | 0 | 0 | 19.3 | 78.4 | 2.3 |
| 3 | 90 | 48 (24)[a] | 0 | 0 | 11.6 | 86.3 | 2.1 |

[a]Additional reaction time at 90° C.

Example 12

Reaction of TMP-ME with DMC

FIG. 10, TMP-monoallyl ether (ME) was dissolved in DMC in 4 mL vial, and reacted by heating with or without molecular sieves (MS) 4A and catalysts ($Na_2CO_3$, or NaOH) using Thermomixer (Table 12). Small aliquots of reaction samples were taken for analysis at varying time intervals. Table 12 shows the results after defined time intervals of the reactions performed under different conditions.

TABLE 12

| Run | TMPME (mg) | DMC (mL) | MS (g) | $Na_2CO_3$ (mg) | Temp (° C.) | Time (h) | starting | 3 | 4 | 5 |
|---|---|---|---|---|---|---|---|---|---|---|
| 1 | 100 | 3 | 0 | 0 | 120 | 24 | 99 | 0 | 1 | 0 |
| 2 | 100 | 3 | 0 | 1 | 120 | 24 | 12.1 | 29.6 | 39.2 | 19.1 |
| 3 | 100 | 3 | 0 | 10 | 120 | 17 | 0.3 | 11.8 | 24.5 | 63.8 |
| 4 | 500 | 1 | 0 | 1 (NaOH) | 120 | 20 | 39.9 | 32.6 | 23.2 | 4.5 |
| 5 | 100 | 3 | 0 | 1 | 120 | 20 | 17.7 | 23.4 | 49.9 | 9 |
| 6 | 100 | 3 | 0.6 | 10 | 80 | 24 | 70.3 | 14.9 | 14.8 | 0 |
| 7 | 100 | 3 | 0 | 0 | 80 | 24 | 73.1 | 15.8 | 11.1 | 0 |
| 8 | 50 | 1 | 0.75 | 0 | 90 | 24 | 0 | 0.3 | 92.5 | 7.2 |

$^1$H-NMR ($CDCl_3$)
Product 4. TMP-ME cyclic carbonate. 0.941 (3H, t), 1.557 (2H, q), 3.425 (2H, s), 4.011 (2H, d), 4.158 (2H, d), 4.365 (2H, d), 5.261 (2H, m), 5.860 (1H, m).

Example 13

Reaction of diTMP with DMC

FIG. 11, 20 g di-trimethylolpropane (di-TMP) was dissolved in 400 mL DMC (2) in 2 L reaction vessel, and reacted by heating with 400 g molecular sieves 4A in 120° C. oil bath for 21 hr. 81.5% yield (GC) of di-TMP dicyclic carbonate (3) was obtained.

$^1$H-NMR ($CDCl_3$)
Product 3. Di-TMP dicyclic carbonate. 0.933 (6H, t), 1.586 (4H, q), 3.518 (4H, s), 4.185 (4H, d), 4.296 (4H, d).

Example 14

Reaction of TMP-MMA with DMC

FIG. 12, 0.5 g trimethylolpropane monomethacrylate (TMP-MMA) was dissolved in 15 mL DMC (2) in 50 mL reaction vessel, and reacted by heating with 6.5 g molecular sieves 4A in 120° C. oil bath for 17 hr. 87.5% yield (GC) of TMP-MMA cyclic carbonate (3) was obtained.

$^1$H-NMR($CDCl_3$)
Product 3. TMP-MMA cyclic carbonate. 0.988 (3H, t), 1.589 (2H, q), 1.976 (3H, s), 4.217 (2H, s), 4.240 (2H, d), 4.348 (2H, d), 5.661 (1H, s), 6.136 (1H, s).

The invention claimed is:

1. A method of producing 6-membered cyclic carbonates comprising the steps of:
   a. providing a polyol and a dialkyl carbonate or a diphenyl carbonate;
   b. forming a mixture of a polyol and dialkyl carbonate or a diphenyl carbonate, said mixture having a dialkyl carbonate or the diphenyl carbonate ratio to the polyol of 0.1-3000 wt %;
   c. optionally adding a solvent;
   d. adding as an adsorbent molecular sieves to said mixture; and
   e. heating the mixture to a temperature of 100° C. or more to obtain 6-membered cyclic carbonates,
   wherein no metal catalyst is used in producing the 6-membered cyclic carbonates, the dialkyl carbonate is dimethyl or diethyl carbonate, and the weight ratio of molecular sieves to polyol is 2:1 or more.

2. The method of claim 1 wherein the mixture is heated to at least the boiling point of the dialkyl carbonate or the diphenyl carbonate.

3. The method according to claim 1 wherein the mixture is heated to 120° C. or more.

4. The method according to claim 3 wherein the mixture is heated to 140° C. or more.

5. The method according to claim 1 wherein the polyol is a C3 or higher tetraol, triol or diol or a C3 or higher tetraol, triol or diol alkyl ester.

6. The method according to claim 1 wherein the polyol is selected from trimethylolpropane, di-trimethylolpropane, pentaerythritol, bis-MPA methyl ester, TMP-monoallylether, TMP-monoacrylate, TMP-monomethacrylate, 1,3-butane diol, 1,4-butane diol or 1,3-propane diol.

7. The method according to claim 1 wherein the solvent is selected from acetonitrile, pyridine and a mixture of THF and toluene or a mixture containing any of said solvents.

8. The method according to claim 1 wherein the molecular sieves are of type 3A, 4A or 5A.

9. The method according to claim 1 wherein the weight ratio of molecular sieves to polyol is 4:1 or more.

10. The method according to claim 1 wherein the weight ratio of molecular sieves to polyol is 6:1 or more.

11. The method according to claim 1 wherein an additional step is performed after step e comprising removing any dialkyl carbonate or diphenyl carbonate and optionally any solvent and heating the remaining mixture at 80° C. or more.

12. The method according to claim 1 wherein no solvent is used.

13. The method according to claim 1 wherein the temperature is 120° C. or more and the weight ratio of molecular sieves to polyol is 4:1 or more.

\* \* \* \* \*